(12) United States Patent
Greenlee et al.

(10) Patent No.: US 11,719,604 B2
(45) Date of Patent: Aug. 8, 2023

(54) FORCEPS WITH REPLACEABLE TIPS

(71) Applicant: SAKURA FINETEK U.S.A., INC., Torrance, CA (US)

(72) Inventors: Joshua Greenlee, Laveen, AZ (US); Erico von Bueren, Lomita, CA (US); Robert Jeffrey Sheppard, Lomita, CA (US)

(73) Assignee: SAKURA FINETEK U.S.A., INC., Torrance, CA (US)

( * ) Notice: Subject to any disclaimer, the term of this patent is extended or adjusted under 35 U.S.C. 154(b) by 280 days.

(21) Appl. No.: 17/368,765

(22) Filed: Jul. 6, 2021

(65) Prior Publication Data

US 2022/0018735 A1 Jan. 20, 2022

Related U.S. Application Data (60) Provisional application No. 63/052,667, filed on Jul. 16, 2020.

(51) Int. Cl.
  *G01N 1/00* (2006.01)
  *G01N 1/08* (2006.01)
  *B25B 9/02* (2006.01)
  *G01N 1/28* (2006.01)

(52) U.S. Cl.
  CPC ............... *G01N 1/08* (2013.01); *B25B 9/02* (2013.01); *G01N 1/286* (2013.01); *G01N 2001/085* (2013.01)

(58) Field of Classification Search
  None
  See application file for complete search history.

(56) References Cited

U.S. PATENT DOCUMENTS

| 2,723,666 A | 11/1955 | Greenberg |
| 3,779,248 A | 12/1973 | Karman |
| 3,818,784 A | 6/1974 | McClure |
| 3,999,434 A | 12/1976 | Yen |

(Continued)

FOREIGN PATENT DOCUMENTS

| GB | 2509110 A | 6/2014 |
| WO | 97/06749 A1 | 2/1997 |

(Continued)

OTHER PUBLICATIONS

Sakura Finetek U.S.A., Inc., Related Application, European Patent Application No. 21184848.6, The Extended European Search Report, dated Nov. 19, 2021.

(Continued)

*Primary Examiner* — Jyoti Nagpaul
(74) *Attorney, Agent, or Firm* — William Thomas Babbitt, Esq.; Leech Tishman Fuscaldo & Lampl, Inc.

(57) ABSTRACT

Handheld forceps comprising: a body comprising trunk and a first arm and a second arm extending from a base of the trunk coupled at one end and separated from one another at a second end; a rod disposed in the body, the rod comprising a first end positioned in the first arm and a second end positioned in the second arm and forming an apex in the trunk; a compression spring disposed around the apex of the rod in the trunk; and a button coupled to the apex of the rod and protruding through an opening in the trunk. Also a method of using the handheld forceps.

7 Claims, 6 Drawing Sheets

(56) References Cited

U.S. PATENT DOCUMENTS

| | | |
|---|---|---|
| 4,343,185 A | 8/1982 | Knute |
| 4,634,165 A | 6/1987 | Russell et al. |
| 4,834,090 A | 5/1989 | Moore |
| 5,250,072 A | 10/1993 | Jain |
| 5,334,215 A | 8/1994 | Chen |
| 5,514,147 A | 5/1996 | Hoskin et al. |
| 6,926,712 B2 | 8/2005 | Phan |
| 8,048,107 B2 * | 11/2011 | Chen ................ A61B 17/30 294/99.2 |
| 10,010,345 B2 | 7/2018 | Mackovic Basic et al. |
| 2017/0100114 A1 | 4/2017 | Scheller et al. |

FOREIGN PATENT DOCUMENTS

| | | |
|---|---|---|
| WO | 1997006749 A1 | 2/1997 |
| WO | WO00/52438 A1 | 9/2000 |
| WO | 03/011152 A1 | 2/2003 |
| WO | 2017/007316 A1 | 1/2017 |

OTHER PUBLICATIONS

Related Application, Sakura Finetek U.S.A., Inc., Canadian Patent Application No. 3,124,746; Examiner's Report; dated Oct. 28, 2022.

Related Application, Sakura Finetek U.S.A., Inc., Japanese Patent Application No. 2021-116882; Notice of Rejection; dated Aug. 15, 2022.

Related Application, Sakura Finetek U.S.A., Inc., Japanese Patent Application No. 2021-116882; Notice of Allowance; dated Nov. 29, 2022.

Related Application, Sakura Finetek U.S.A., Inc., Australian Patent Application No. 2021204835; Examination Report No. 1, dated Jun. 30, 2022.

* cited by examiner

FORCEPS WITH REPLACEABLE TIPS

FIELD

Forceps and replaceable tips for forceps

BACKGROUND

Pathology grossing tools are known in the art for preparing a tissue sample, which was obtained by excision/resection of a body part or biopsy, to process for histology, genetic analysis, histochemistry, or the like. One grossing tool is a forceps, particularly thumb forceps. Thumb forceps are forceps that have two arms (pincers) that typically are connected at one end and their opposite end defines a pair of opposed grasping ends. Thumb forceps are typically held between the thumb and two or three fingers on one hand. Spring tension at the connected end holds the grasping ends apart until pressure is applied by the thumb and fingers to bring the grasping ends together to grasp small objects or tissue to move and hold or release the tissue.

DETAILED DESCRIPTION

Handheld forceps and their use are disclosed. Specifically, handheld forceps that may accommodate replaceable tips at their grasping ends are disclosed. The handheld forceps include a body comprising a trunk and a first arm and a second arm extending from a base of the trunk coupled at one end and separated from one another at a second end. A rod is disposed in the body and the rod includes a first end positioned in the first arm and a second end positioned in the second arm. The rod conforms to a shape of the trunk to define an apex in the trunk. A compression spring is disposed in the trunk around the apex of the rod. A button is connected to the apex of the rod and protrudes through an opening in the trunk. A replaceable (e.g., disposable) tip may be placed on an end of each of the first arm and the second arm. The button may be depressed to advance the rod toward the arms to cause a displacement or ejection of the tips from the arms. In this manner, the tips may be removed without direct physical contact. The replaceable tip feature allows the forceps to be used repeatedly, such as for different grossing applications in a pathology laboratory.

FIGS. 1-11 show handheld forceps or portions thereof that are suitable for use in grossing applications in a pathology laboratory. Referring to FIG. 1, FIG. 2, FIG. 8 and FIG. 9, forceps 100 include body 110 that includes trunk 115 from which arm 120 and arm 125 extend. Trunk 115 and arms 120 and 125 may be made of a durable material such as carbon steel, such as stainless steel or plastic.

Trunk 115 of handheld forceps 100 may have a generally tubular shape and may be generally hollow or at least define an interior volume or space. A superior or top surface of trunk 115 defines opening 118 into the volume or space. Trunk 115 may be formed of a single unit or from two halves that come together to form a single unit with bonding (e.g., adhesive, weld). Opposite faces of trunk 115 may include aligned openings or slots 117 that may serve to define a travel of a button inserted through opening 118 as described below.

Figure 8:
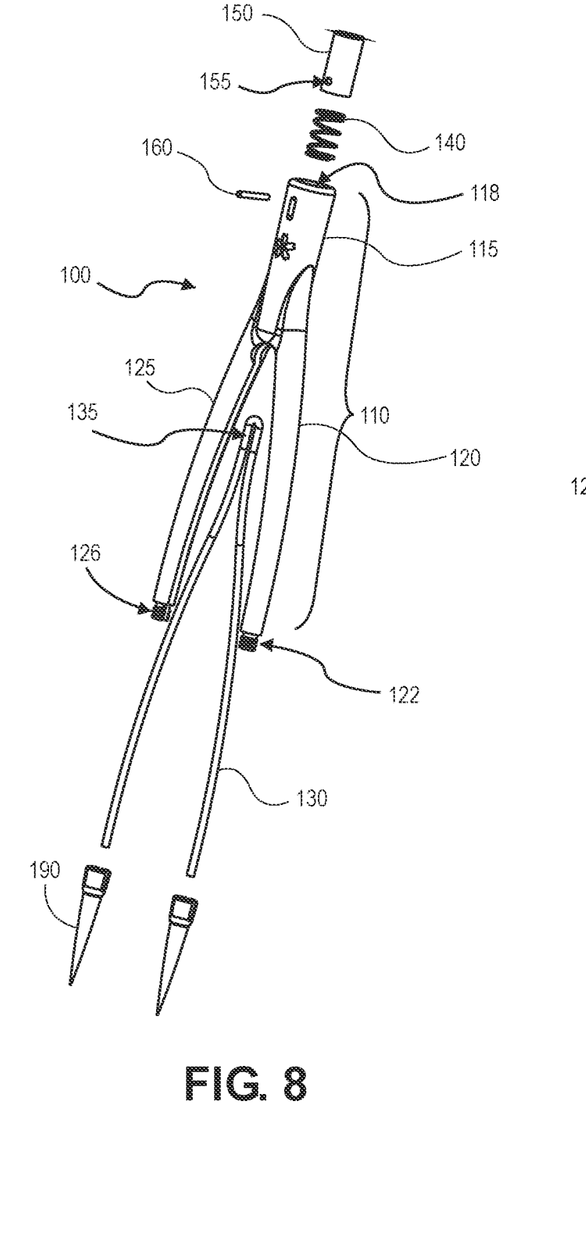
FIG. 8 shows an exploded view of the forceps of FIG. 1 without sleeves on the arms of the forceps.
Figure 9:
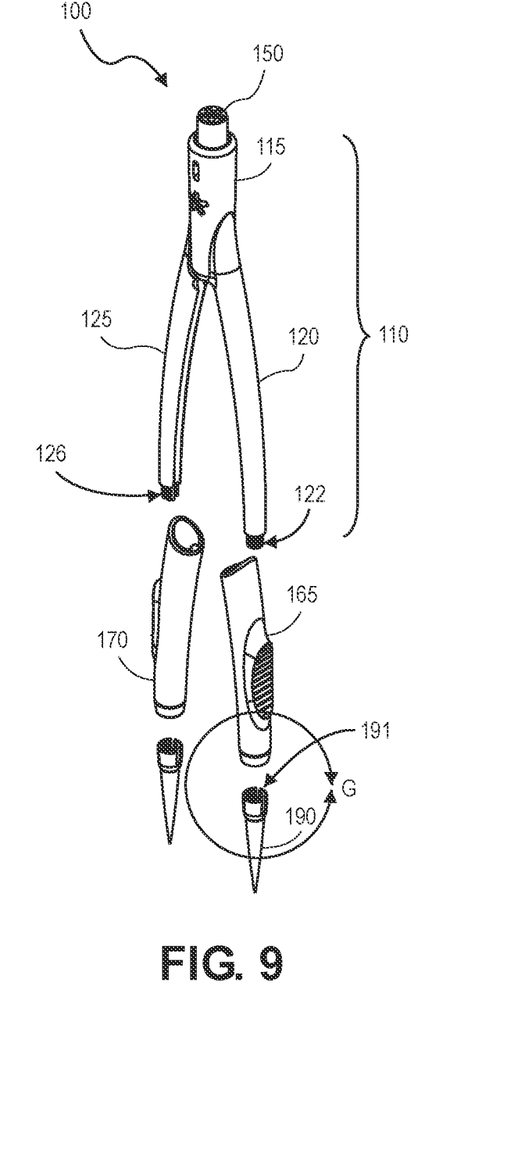
FIG. 9 shows an exploded view of the forceps of FIG. 1 without a rod.

As viewed, arms 120 and 125 extend from a base of trunk 115 and at opposite sides of the trunk. Arms 120 and 125 may be connected to trunk 115 by bonding (e.g., welding). In an open position as shown in the figures, each of arm 120 and arm 125 projects away from a base of trunk 115 at an angle, such as an angle of 20° to 30° from an axis of trunk 115 (the axis indicated by a dashed line in FIG. 1). Arms 120 and 125 are oppositely opposed in a manner that an inward directed force directed on one can bring the arm toward the axis and toward the other arm to define a closed or grasping position. Removing the force causes the arm to return to the open position. Arm 120 and arm 125 may be constructed such that the force to move from an open to closed position can be applied by fingers of the human hand. Arm 120 and arm 125 may have a generally tubular shape and may be generally hollow or have a u-, v- or parabolic-shape where the opening (the apex of the u-, v- or parabolic-shape) in one arm projects in a direction toward the opening in the other arm. FIG. 8 and FIG. 9 show arms with the described u-, v- or parabolic-shape. A base or distal end portion of arm 120 and arm 125 (distal from trunk 115) may include ridges or axial protrusions. FIG. 8 and FIG. 9 show ridges or axial protrusions 122 on arm 120 near an end portion of the arm and ridges or axial protrusions 126 on arm 125 also near an end portion. Ridges or axial protrusions 122 and 126 provide resistance or traction for tips to be placed (e.g., manually placed) on arms 120 and 125 as described below. The end portion of arms 120 and 125 may also include a protruding tab or key near an end portion of the arm (see longitudinally extending tab or key 129 in FIG. 3). Tab or key 129 may provide a directional orientation for a tip placed on an arm so that the tip is placed in a correct orientation relative to the arm and remains in that orientation through a use of the forceps.

Disposed on arm 120 is sleeve 165 and disposed on arm 125 is sleeve 170. Each of sleeve 165 and 170 may be a deformable plastic material (e.g., polypropylene) that has a tubular shape that can be placed over a respective arm in a form fit to conform to the shape of the arm. Sleeve 165 and sleeve 170 may provide a cushion to fingers when using forceps 100.

Figure 1:
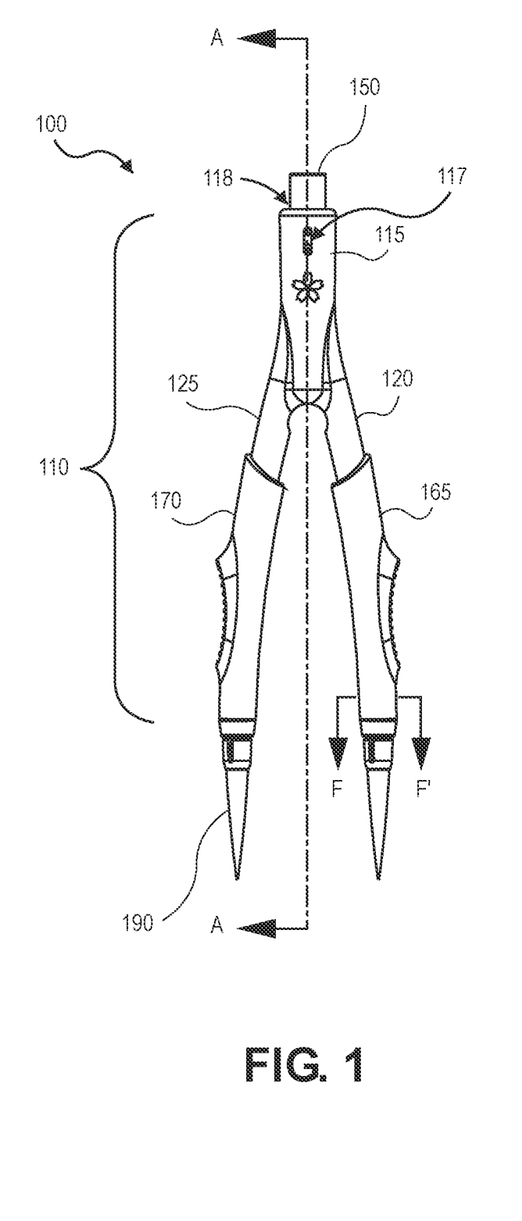
FIG. 1 shows a front view of a handheld forceps.
Figure 2:
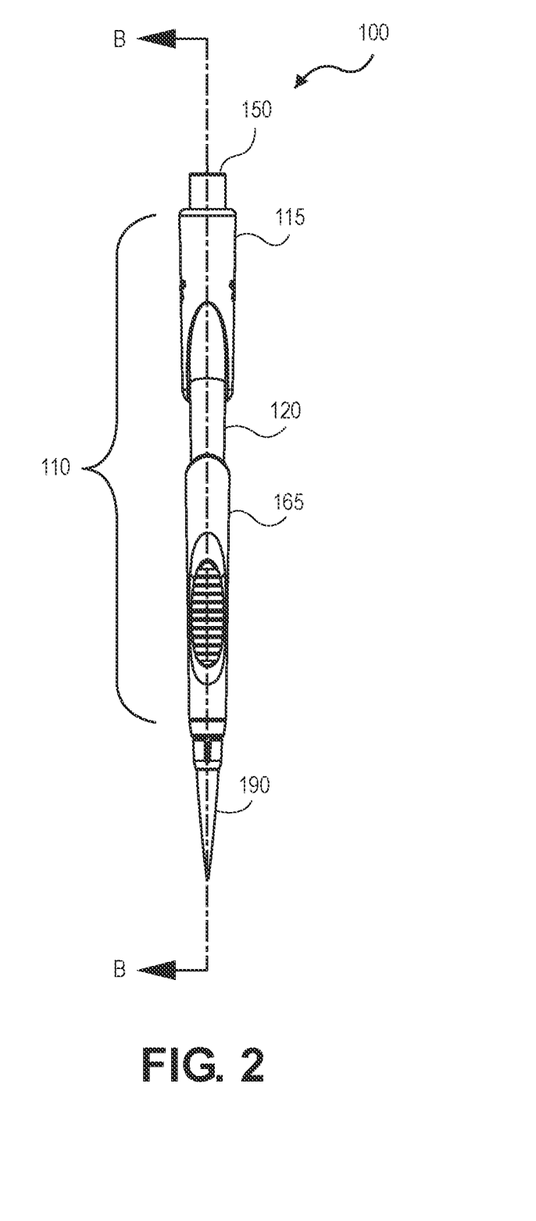
FIG. 2 shows a side view of the forceps of FIG. 1.
Figure 3:
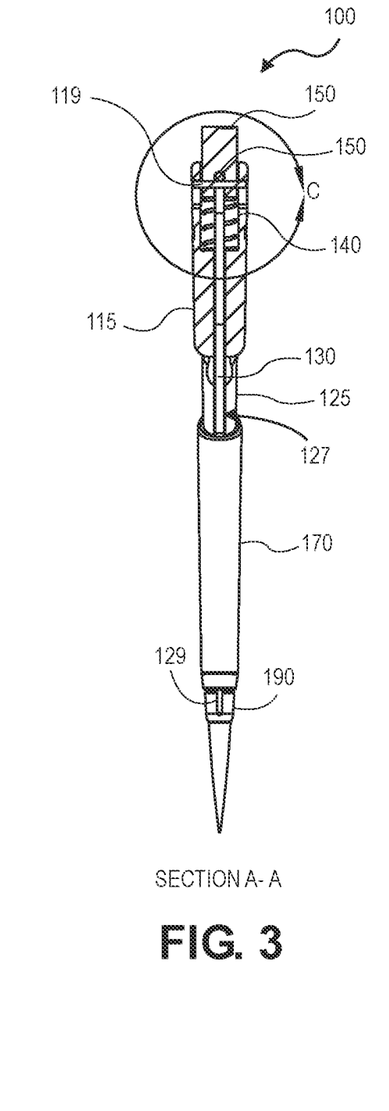
FIG. 3 shows the forceps of FIG. 1 through line A-A' of FIG. 1.
Figure 4:
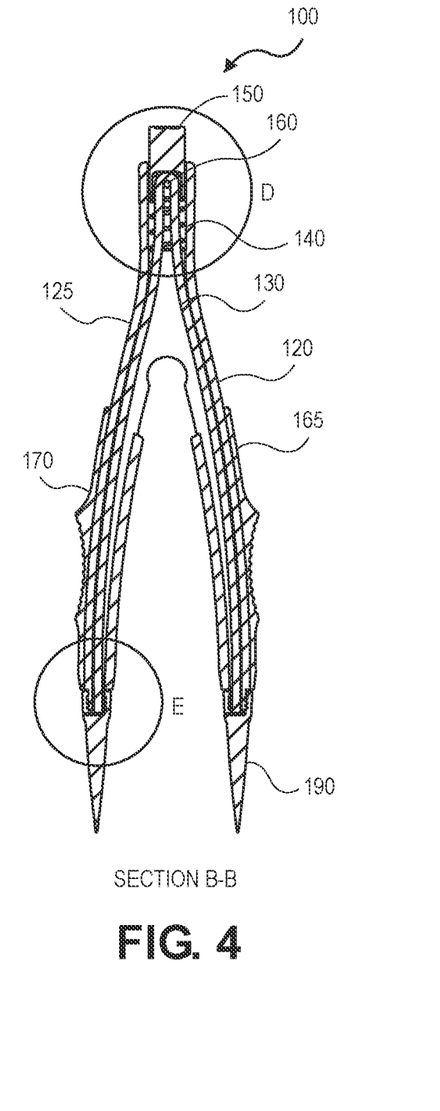
FIG. 4 shows the forceps of FIG. 1 through line B-B' of FIG. 2.
Figure 7:
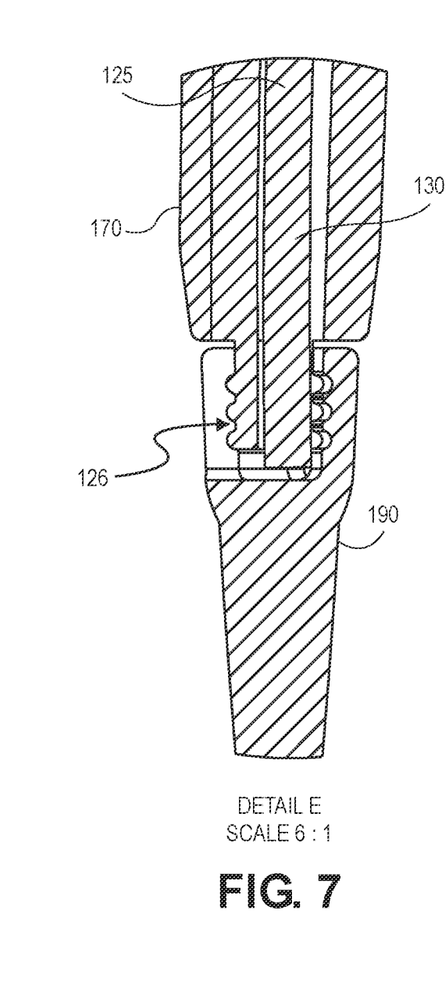
FIG. 7 shows the forceps of FIG. 1 and shows Detail E in FIG. 4.
Figure 10:
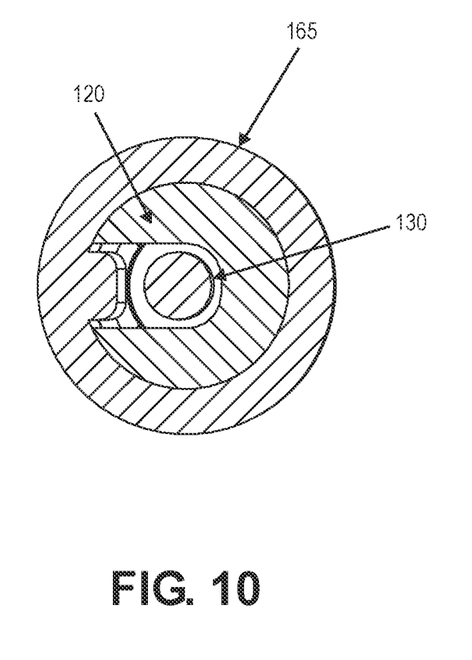
FIG. 10 shows a cross-section through line F-F' of the forceps in FIG. 1.

As shown in FIG. 4, FIG. 8 and FIG. 9, disposed in body 110 (in trunk 115 and arms 120 and 125) of forceps 100 is rod 130. Rod 130 has a first end positioned in arm 120 and a second end positioned in arm 125. Rod 130 has a shape that conforms to a shape of the body of forceps 100 so that a middle section or portion of the rod is disposed in trunk 115. A midpoint of rod 130 defines an apex at an approximately 180° bend in the rod in trunk 115. Where arm 120 and arm 125 have a u-, v- or parabolic-shape, rod 130 may be positioned in the respective arms through the opening therein and then the middle section or portion of rod 130 may be pushed (e.g., upwardly) into trunk 115. Where trunk 115 is a two-piece unit, a middle section or portion of rod 130 may be positioned in trunk 115 before the pieces of trunk 115 are bonded together. FIG. 10 shows a cross-section through line F-F' in FIG. 1 and illustrates arm 120 having a u-, v- or parabolic-shape (e.g., a backward c-shape) with rod 130 positioned in the opening therein. As shown in FIG. 4 and FIG. 7, when installed in body 110, rod 130 may have a length such that its ends are as long or slightly longer than a length of arms 120 and 125, respectively. FIG. 4 and FIG. 7 show an example where the ends of rod 130 protrude slightly (e.g, about 10-20 millimeters) beyond each end of arm 120 and arm 125.

Figure 5:
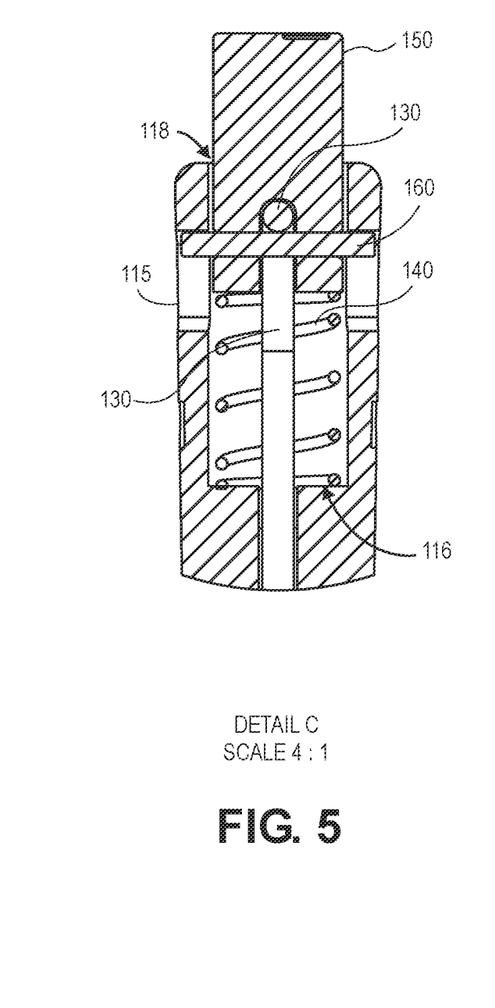
FIG. 5 shows the forceps of FIG. 1 and shows Detail C in FIG. 1.
Figure 6:
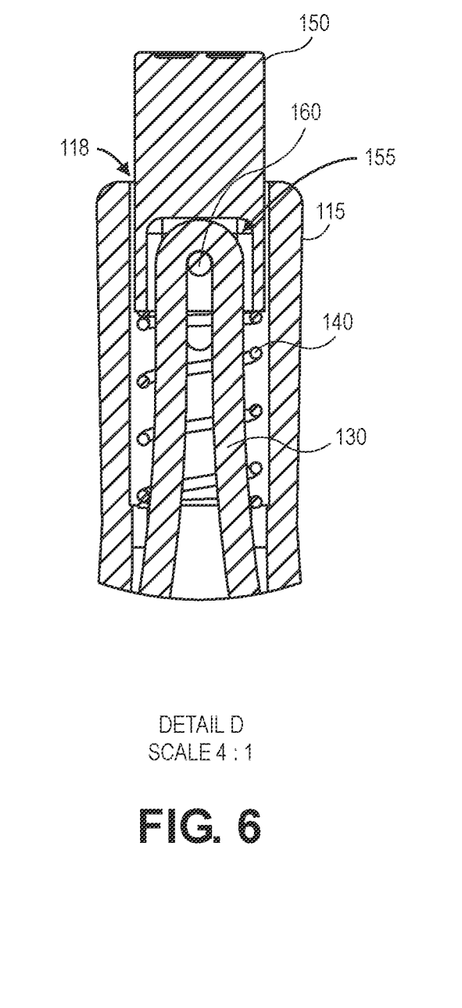
FIG. 6 shows the forceps of FIG. 1 and shows Detail D in FIG. 4.

Positioned around a portion of the middle section on portion of rod 130 is compression spring 140. Compression spring 140 may be a durable material such as steel. Once rod 130 is placed in trunk 115, compression spring 140 may be introduced through opening 118 and surround rod 130. As shown in FIG. 5 and FIG. 6, trunk 115 includes an inwardly protruding shelf 116 that forms a stop for a base of spring 140. Shelf 116 may be bisected on opposite sides to define two oppositely opposing shelves to accommodate rod 130 on each side of the shelf (shelves) as shown in FIG. 5 and FIG. 6.

Positioned in opening 118 of trunk 115 is button 150. Button 150 may be generally cylindrical solid unit of a durable material such as carbon steel or a hard plastic. A base of button 150 includes groove or notch 155 sized to accommodate a portion of the middle section or portion of rod 130 including the midpoint of rod 130 as illustrated in FIG. 5 and FIG. 6. Once rod 130 is positioned in trunk 115, button 150 may be introduced into opening 118 of trunk 115 a distance to capture a portion of the middle section on portion of rod 130. A base of button 150 contacts a top surface of spring 140. Pin 160 of a durable material such as carbon steel may then be inserted through opening or slot 117 in trunk 115. Pin 160 extends laterally through the bend in rod 130 to retain rod 130 in opening or slot 155 (see FIG. 6). Pin 160 may have a length such that its ends extend through openings or slots 117 in trunk 115. Depressing a top surface of button 150 toward opening 118 (e.g., a downward force) with, for example, a thumb or finger, causes the button and rod 130 to move from a first position in the trunk downward in trunk 115 to a second position with resistance from compression spring 140. The downward movement is limited to a length of openings or slots 117 in trunk 115. Rod 130 is biased to the first position by spring 140 so that releasing pressure on button 150 causes rod 130 to return to the first position and button 150 to return to its undepressed position.

Figure 11:
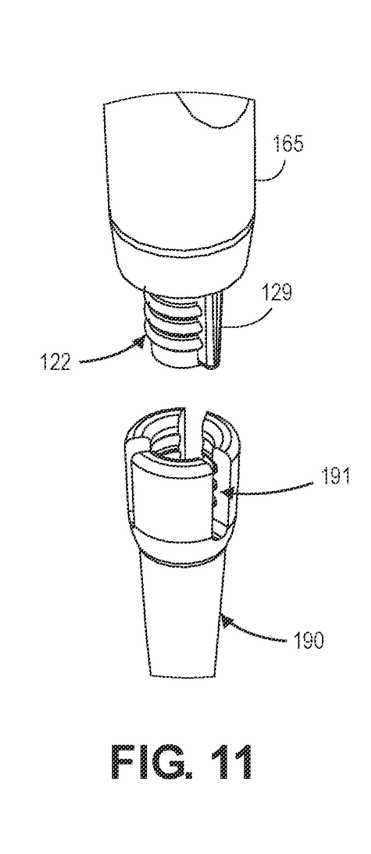
FIG. 11 shows an exploded view of the end of an arm of the forceps of FIG. 1 and shows a tab or key extending a length of axial protrusions and able to mate with a groove in a tip.

Forceps 100 are designed to accommodate manually installed tips on the end of each of arm 120 and arm 125. The design allows the tips to be removed after a use or uses and replaced. FIGS. 1-4, 7 and 8-9 show tips 190. Tips 190 may be a durable plastic material that have a shape at a superior or upper end that has an opening that conforms to a shape of an end of arm 120 and arm 125. An opposite end may have a rectangular (spade) shape, point, or other shape depending on the intended use for the forceps. A tip is placed on arm 120 or arm 125 by pushing the tip onto the arm and over ridges or axial protrusions 122 on arm 120 or ridges or axial protrusions 126 on arm 125. Ridges or axial protrusions 122 and 126 serve to secure tips 190 on the arms (see FIG. 7). Each tip may have opening or groove 191 (see FIG. 9) to mate with a tab or key on the end portion of the arm (e.g., tab or key 129, FIG. 3) to orient the tip on an arm. FIG. 11 shows an exploded view of the end of arm 120 and shows tab or key 129 extending a length of axial protrusions 122 and able to mate with groove 191 (having a width and length dimension similar to tab or key 129) in tip 190. With the tips installed, forceps 100 may have a representative length on the order of 10 centimeters (cm) to 20 cm, such as 12 cm to 15 cm and a representative width at its base in an open position (with neither of arm 120 or arm 125 pressed toward the other) of 1 cm to 4 cm, such as 2 cm to 3 cm.

To remove tips 190 from respective ones of arm 120 and arm 125, a user of forceps 100 depresses button 150 (e.g., with a thumb or finger). Depressing button 150 advances rod 130 downward. The downward advancement of rod 130 cause the ends of the rod to apply a force on tips 190 and push tips off of the end of arms 120 and 125 (e.g., the force is sufficient to overcome the elastic attachment provided by ridges or axial protrusions 122 and 126 on the arms). Once the tips are pushed off the ends of arm 120 and arm 125, the depression force on button 150 may be released and compression spring 140 will advance rod 130 into a position where tips 190 may be installed on arms 120 and 125.

Figure 12:
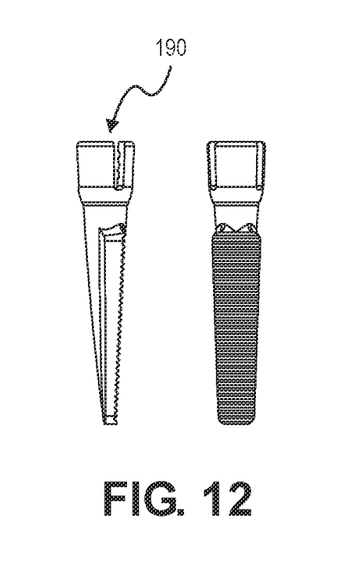
FIG. 12 shows a serrated tip that may be connected to an arm of the forceps in FIG. 1.
Figure 13:
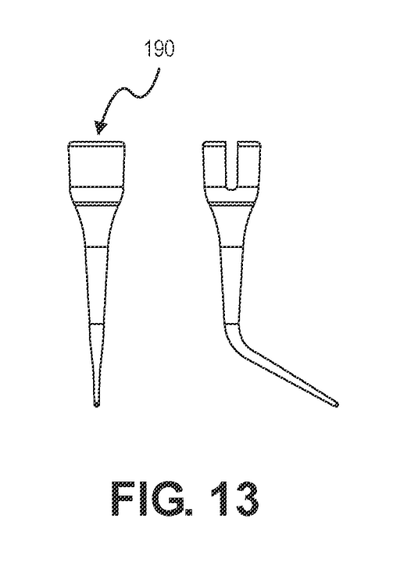
FIG. 13 shows a grossing tip that may be connected to an arm of the forceps in FIG. 1.

FIGS. 12 and 13 show examples of tips 190 that may be used with forceps 100. FIG. 12 and FIG. 13 show front and side views of tips 190. FIG. 12 shows a serrated tip and FIG. 13 shows a grossing tip. It is appreciated that these are two examples of suitable tips and that forceps 100 may accommodate tips having other shapes or properties.

Aspects

Aspect 1. Handheld forceps including:

a body comprising a trunk and a first arm and a second arm, wherein each of the first arm and the second arm are coupled at a first end to the trunk and extend from a base of the trunk and are separated from one another at a second end;

a rod disposed in the body, the rod comprising a first end positioned in the first arm and a second end positioned in the second arm and forming an apex in the trunk;

a compression spring disposed around the apex of the rod in the trunk; and a button coupled to the apex of the rod and protruding through an opening in the trunk.

Aspect 2. The handheld forceps of Aspect 1, wherein the trunk comprises a volume therein defined by the opening at its end and a shelf, wherein one end of the compression spring contacts the shelf and wherein the button is disposed around the spring.

Aspect 3. The handheld forceps of Aspects 1 or 2, wherein the rod has a first position wherein the first end and the second end are operable with the arms to accept a tip on the end of the respective first end and respective second end and a second position operable to separate the tip from the respective first end or second end.

Aspect 4. The handheld forceps of Aspect 3, wherein in the second position, the first end and the second end of the rod are disposed a greater distance from a respective end of the first arm and the second arm.

Aspect 5. The handheld forceps of Aspect 3, wherein the rod is operable to move from the first position to the second position by the depression of the button toward the opening in the trunk.

Aspect 6. The handheld forceps of Aspect 3, wherein the rod is biased to the first position by the compression spring.

Aspect 7. A method of using handheld forceps of any of Aspects 1-6, comprising: pushing a first tip onto the first arm and a second tip onto the second arm of the body; and depressing the button to cause the rod to move the first tip off of the first arm and the second tip off of the second arm.

Whereas specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims and aspects appended and any and all equivalents thereof.

What is claimed is:

1. Handheld forceps comprising:
    a body comprising trunk and a first arm and a second arm extending from a base of the trunk coupled at one end and separated from one another at a second end;
    a rod disposed in the body, the rod comprising a first end positioned in the first arm and a second end positioned in the second arm and forming an apex in the trunk;
    a compression spring disposed around the apex of the rod in the trunk; and
    a button coupled to the apex of the rod and protruding through an opening in the trunk.

2. The handheld forceps of claim 1, wherein the trunk comprises a volume therein defined by the opening at its end and a shelf, wherein one end of the compression spring contacts the shelf and wherein the button is disposed around the spring.

3. The handheld forceps of claim 1, wherein the rod has a first position wherein the first end and the second end are operable with the arms to accept a tip on the end of the respective first end and respective second end and a second position operable to separate the tip from the respective first end or second end.

4. The handheld forceps of claim 3, wherein in the second position, the first end and the second end of the rod are disposed a greater distance from a respective end of the first arm and the second arm.

5. The handheld forceps of claim 3, wherein the rod is operable to move from the first position to the second position by the depression of the button toward the opening in the trunk.

6. The handheld forceps of claim 3, wherein the rod is biased to the first position by the compression spring.

7. A method of using handheld forceps of claim 1, comprising:
    pushing a first tip onto the first arm and a second tip onto the second arm of the body; and
    depressing the button to cause the rod to move the first tip off of the first arm and the second tip off of the second arm.

* * * * *